United States Patent [19]

Yates

[11] 4,163,692

[45] Aug. 7, 1979

[54] LOW PHOSPHATE GROWTH OF FUNGAL MYCELIA

[75] Inventor: Richard A. Yates, Wilmington, Del.

[73] Assignee: E. I. Du Pont de Nemours and Company, Wilmington, Del.

[21] Appl. No.: 790,855

[22] Filed: Apr. 25, 1977

[51] Int. Cl.$^2$ .................. C12B 1/08; C12D 13/06
[52] U.S. Cl. .................. 435/254; 426/656; 435/929; 435/270
[58] Field of Search .............. 195/32, 81, 115, 117, 195/5, 35; 426/48, 60, 656

[56] References Cited

U.S. PATENT DOCUMENTS

| | | | |
|---|---|---|---|
| 2,686,754 | 8/1954 | Monod | 195/115 |
| 3,865,951 | 2/1975 | Spicer | 426/60 |
| 3,937,654 | 2/1976 | Solomons et al. | 195/35 |
| 3,937,693 | 2/1976 | Towersey et al. | 260/112 R |
| 4,041,189 | 8/1977 | Towersey et al. | 426/656 |

OTHER PUBLICATIONS

Oliveria, "Reduction of Nucleic Acids Content of 'Candida utilis' Yeast," *Ind. Aliment. Agr.*, (1976), pp. 689–693.

Sinskey et al., "Removal of Nucleic Acids in SCP," *Single-Cell Protein II*, Tannenbaum et al., ed, The MIT Press, Cambridge (1975), pp. 158–178.

*Primary Examiner*—Thomas G. Wiseman

[57] ABSTRACT

Fungal mycelia are grown in a medium wherein the phosphate level is only slightly above the level which will limit growth, which results in a slightly lower content of ribonucleic acid in the mycelia but which results in the cells being much more amenable to removal of ribonucleic acid by simple means such as thermal shock.

7 Claims, No Drawings

LOW PHOSPHATE GROWTH OF FUNGAL MYCELIA

BACKGROUND OF THE INVENTION

Recent concern for the welfare of the world population has included consideration of additional means for feeding the rapidly increasing number of people involved. The problem embraces providing both adequate per capita caloric intake and a balanced diet, with particular reference to the lack of protein affording foods in many parts of the world. One means for providing necessary protein supplies is through the growth of fungal mycelia for use either as food or food supplements.

Production of edible fungal mycelia in large quantities may be accomplished by fermentation processes employing a carbohydrate substrate. The principal requirements are that the substrate material be relatively inexpensive and readily consumed by the selected microorganism.

The human metabolic system produces uric acid in the metabolism of ribonucleic acid. Since man does not have a uricase enzyme system, uric acid is not further broken down and is excreted in the urine. Because uric acid salts have a very low solubility in biological fluids, they will accumulate in the body in crystalline form if produced in larger quantities than the body can excrete. This may lead to the condition known as gout. For this reason nutritionists recommend that the ribonucleic acid intake in diet be kept at a low level.

Fungal mycelia generally contain from 7 to 9% nucleic acids. If the fungal mycelia are to be used as a protein source in human feeding, nutritionists generally recommend that the amount of nucleic acids contributed by single cell protein or fungal mycelia should not exceed 2 grams per day.

A preferrred way of utilizing edible fungal mycelia is in the form of whole cells. Accordingly, there is a need for a means for removing nucleic acids from within the fungal mycelia. This desirably is accomplished with a minimum loss of protein material from within the cells in order to maintain the nutritional attractiveness of such fungal mycelia. One method found to work well with some fungi in reducing nucleic acid content is the isothermal shock method disclosed in U.S. Pat. No. 4,041,189 Any procedure permitting increased effectiveness of this procedure should therefore decrease the possibility of gout when processed fungal material is used as human food.

SUMMARY OF THE INVENTION

The present invention involves growing fungal mycelia in a medium wherein the phosphate level is only slightly above the level which will limit growth of the mycelia. The thus grown fungal mycelia have been more amenable to loss of ribonucleic acid upon processing.

DESCRIPTION OF THE INVENTION

According to the present invention there is provided a process for the production of edible protein containing fungal mycelia which comprises incubating and proliferating, under aerobic conditions, non-toxic strains of fungi in a culture medium containing essential growth-promoting nutrient substances and separating the proliferated mycelia.

The separated proliferated fungal mycelia after reduction of the ribonucleic content thereof are suitable for use as a human foodstuff. The preferred fungi for use in the present invention are Fungi Imperfecti of the genus Fusarium with *Fusarium graminearum* Schwabe being especially preferred. The most preferred microfungus is *Fusarium graminearum* Schwabe deposited with the Commonwealth Mycological Institute (I.M.I.) and the American Type Culture Collection and assigned the numbers I.M.I. 145,425 and A.T.C.C. 20,334. Suitable reisolates of this microfungus also deposted with the Commonwealth Mycological Institute and the American Type Culture Collection include I.M.I. 154,209, A.T.C.C. 20,329; I.M.I. 154,210, A.T.C.C. 20,333; I.M.I. 154,211, A.T.C.C. 20,330; I.M.I. 154,212, A.T.C.C. 20,331; I.M.I. 154,213, A.T.C.C. 20,332. Other suitable nontoxic microfungi include but are not limited to Fusarium Oxysporum (I.M.I. 154,214, A.T.C.C. 20,328), and Fusarium Solani (I.M.I. 154,217, A.T.C.C. 20,327), with the numbers of strains thereof which have been deposited with the Commonwealth Mycological Institute and the American Type Culture Collection given in parenthesis.

The present invention is based on the discovery that when fungal mycelia are grown under aerobic conditions in a culture medium containing essentially growth-promoting nutrient substances wherein the mycelia cells are partly starved of phosphate, the cells are more readily amenable to the reduction of their ribonucleic acid (etc) content. The net effect is an enhanced reduction in residual nucleic acid in the product, thus a product with more desirable properties as a human food source.

Generally, the amount of phosphate present in the medium should be from the level where phosphate is the growth limiting factor in the fermenter composition up to 5 millimolar above the growth limiting level. For *Fusarium graminearum* Schwabe A.T.C.C. 20,334 grown at 20 g/l. this growth limiting level of phosphate has been found to be about 6 millimolar. For this particular Fusarium a phosphate concentration in the initial medium of from 7 to 10 millimolar has been found to give the best results.

The preferred ribonucleic acid reduction is by enzyme activation. The preferred enzyme activation is by thermal shock. Generally, this is done by maintaining the fungal mycelial mass in an aqueous suspension at a pH of from 4.7 to 7.0 at a temperature of about 64° for a time of about 15 minutes. The process of this isothermal shock has been reported in U.S. Ser. No. 507,123 and is not claimed in this invention. The grown fungal mycelia are harvested, and filtered to remove growth medium, if desired. The fungal mycelia are then brought rapidly to the desired temperature with an aqueous buffer solution in the range of pH 4.7 to 7.0. An alternate approach would be to heat the whole mycelia culture slurry rapidly. The resulting treated fungal mycelia mass may then be harvested again, for example, by filtration and washing with water and thereafter formulated into foods. In the case of the preferred *Fusarium graminearum* Schwabe A.T.C.C. 20,334 ribonucleic acid content can readily be reduced to below 0.5 weight percent (5 milligrams per gram of mycelia dry basis) using this very easily carried out thermal enzyme activation.

EXAMPLES

A continuous 8-liter fermenter is sterilized and continuously charged with a sterile medium consisting of

| | g per 100 liters |
|---|---|
| $MgSO_4$ | 50 |
| $ZnSO_4 . 7H_2O$ | 0.83 |
| $CuSO_4 . 5H_2O$ | 0.167 |
| $MnSO_4 . 1H_2O$ | 0.63 |
| $FeSO_4 . 7H_2O$ | 0.62 |
| $K_2SO_4$ | 10.0 |
| $(NH_4)_2SO_4$ | 144.0 |
| $NaMoO_4 . 2H_2O$ | 0.083 |
| $CoCl_2 . 6H_2O$ | 0.17 |
| NaCl | 1.0 |
| $CaCl_2$ | 8.0 |
| Biotin | 0.0006 |
| Dextrose . $H_2O$ (carbohydrate) | 5,000.0 |
| Ammonium citrate | 4.0 |
| Boric acid | 0.05 |
| $KH_2PO_4$ | as reported in Table I |
| Water | to 100 liters |

The rate of charging the sterile medium is 1.3 liters per hour. The medium is inoculated with a spore suspension of *Fusarium graminearum* Schwabe I.M.I. 145,425, A.T.C.C. 20,334. The fermenter is stirred with a 6-bladed disc turbine operated at 750 rpm. Air is flowed through the fermenter at a rate of 3.6 liters per minute. Additional oxygen flow is 2.0 liters per minute. The fermenter temperature is 29.2° C., and the pH is 4.8. Ammonia is added to control the pH and provide additional mycelial nutrient. The fermenter productivity is about 3 $gl^{-1}hr^{-1}$. The product fungal mycelium is continuously drawn off the fermenter, and collected in a product receiver which is held at 8° C. After steady operation is achieved the pooled product for about 10 hours operation is then harvested. The resultant filter cake is then suspended in 8.0 liters of filtrate which has been preheated to 72° C. and adjusted to pH 6.0 with NaOH. Addition of the filter cake to the heated filtrate decreases the slurry temperature to 64° C. which is then maintained for 20 minutes. This treatment serves to reduce the ribonucleic acid content of the filter cake. The slurry is then filtered and washed on the filter bed with one half the bed volume of distilled water. The filter cake is then dewatered with a vacuum to a solids content of 27.6 weight percent. At this point the wet filter cake comprises an entangled mass of limp flexible mycelial filaments. Samples of the fungal mycelia are analyzed for α-aminonitrogen and ribonucleic acid before and after reduction of ribonucleic acid (RNA). The "yield" reported in Table I is determined by dividing the fermenter cell mass by the glucose used. Typical control run yields are about 0.5.

TABLE I

| Code | Initial Concen. Phosphate, mM | Approx. Residual Phosphate | Typical Run hour | Fresh A3/5 Exfermenter αAN | RNA | Cell Mass g/l | RNA reduced product Mg/g αAN | RNA | Yield |
|---|---|---|---|---|---|---|---|---|---|
| Control | 28mM | (21) | 85 | 69.5 | 90.0 | 29 | 72 | 16. | |
| Run 1 | 7.0 | 2 | 62 | 64.3 | 88.4 | 20.1 | | | |
| | 4.0 | <1 | 85 | 59.6 | 63.2 | 15.9 | | | |
| | 6.0 | 1 | 103 | 64.9 | 77.1 | 19.4 | | | |
| | 6.0 | <1 | 111 | 50.9 | 52.1 | 27.0 | 67.9 | 3.5 | 0.49 |
| | 8.0 | 2 | 158 | 62.0 | 75.3 | 24.7 | | | 0.52 |
| | 7.0 | 1 | 203 | 61.2 | 70.0 | 23.5 | 70.7 | 2.8 | 0.50 |
| | 7.5 | 2 | 213 | 62.8 | 79.4 | 22.3 | 69.7 | 2.2 | 0.52 |
| | 9.0 | 3 | 230 | 62.8 | 80.0 | 24.4 | 70.5 | | 0.53 |
| | 6.0 | 1 | 248 | 61.7 | 74.6 | 20.1 | 66.6 | 3.4 | 0.50 |
| | 28.0 (starting at hour about 265) | 23 | 278 | 64.4 | 85.6 | 20.8 | 68.2 | 6.7 (rising) | |
| Run 2 | 7.0 | 2.5 | 81 | 61.7 | 80.1 | 17.6 | 68.6 | 3.7 | |
| | 7.0 | 2.5 | 155 | 63.5 | 82.1 | 17.0 | 69.0 | 4.9 | |

As can be seen the use of low phosphate in the fermenter in accordance with the present invention results in a greatly lowered amount of ribonucleic acid in the treated product without a significant loss of protein as evidenced by the α-aminoacid analysis (αAN).

I claim:

1. A process comprising growing an edible strain of Fusarium on a carbohydrate substrate under aerobic conditions in a culture medium containing essential growth-promoting nutrient substances to produce a mycelial mass, wherein the phosphate present in the medium is maintained at from the amount which is growth limiting up to 5 millimolar above the amount which is growth limiting, harvesting at least a portion of the grown fungal mycelial mass and reducing the ribonucleic acid content of the harvested fungal mycelial mass by means of enzyme activation.

2. The process of claim 1 wherein the reduction of ribonucleic acid is effected by maintaining the fungal mass in an aqueous suspension at a pH between 4.7 and 7.0 at a temperature between 55° and 72° C. for a time of at least 60 seconds.

3. The process of claim 2 wherein the strain of Fusarium is a strain of *Fusarium graminearum* Schwabe, *Fusarium oxysporum*, or *Fusarium solani.*

4. The process of claim 3 wherein the strain of Fusarium is a strain of *Fusarium graminearum* Schwabe.

5. The process of claim 4 wherein the concentration of the strain of Fusarium is maintained at from 15 to 25 grams per liter and the phosphate level in the fermenter is maintained at from 7 millimolar to 10 millimolar.

6. The process of claim 5 wherein the ribonucleic acid reduction step is performed by rapidly raising the temperature of the fungal mycelial mass at least 25° C. to from 55° to 72° C. and a product containing less than 0.5 weight percent ribonucleic acid is obtained.

7. The process of claim 6 wherein the *Fusarium graminearium* Schwabe is derived from strain A.T.C.C. 20,344.

* * * * *